United States Patent [19]

Collins et al.

[11] 4,340,390
[45] Jul. 20, 1982

[54] METHOD AND APPARATUS FOR METERING BIOLOGICAL FLUIDS

[75] Inventors: Richard A. Collins, Fairport; Glenn E. Tersteeg, Honeoye Falls; Thomas C. Jessop, Webster, all of N.Y.

[73] Assignee: Eastman Kodak Company, Rochester, N.Y.

[21] Appl. No.: 260,855

[22] Filed: May 6, 1981

Related U.S. Application Data

[63] Continuation-in-part of Ser. No. 159,563, Jun. 16, 1980, abandoned.

[51] Int. Cl.³ .......................... G01N 1/14; G01N 1/28
[52] U.S. Cl. .................................. 23/230 B; 141/130; 422/63; 422/64; 422/100
[58] Field of Search .......................... 23/230 R, 230 B; 422/63, 64, 65, 66, 100; 141/130; 73/425.6

[56] References Cited

U.S. PATENT DOCUMENTS

| | | | |
|---|---|---|---|
| 3,219,416 | 11/1965 | Natelson | 23/253 |
| 3,261,668 | 7/1966 | Natelson | 23/253 |
| 3,570,555 | 3/1971 | Gilson | 141/1 |
| 3,576,605 | 4/1971 | Drake et al. | 422/65 X |
| 3,687,632 | 8/1972 | Natelson | 23/259 |
| 3,739,821 | 6/1973 | Watkin et al. | 141/392 |
| 3,991,627 | 11/1976 | Laird et al. | 73/423 R |
| 4,004,883 | 1/1977 | Meyer et al. | 23/259 |
| 4,046,511 | 9/1977 | Stabile | 23/259 |
| 4,161,508 | 7/1979 | Janchen | 422/100 |
| 4,166,483 | 9/1979 | Nordlund | 141/1 |
| 4,257,862 | 3/1981 | Schnipelsky et al. | 422/63 X |
| 4,269,803 | 5/1981 | Jessop | 422/63 |

Primary Examiner—Ronald E. Serwin
Attorney, Agent, or Firm—D. D. Schaper

[57] ABSTRACT

A method and apparatus are disclosed for repeatedly and accurately depositing predetermined amounts of fluid, especially biological fluids, onto generally planar analysis slides. The apparatus comprises a dispenser which is adapted to pick up a disposable metering tip, aspirate fluid into the tip, meter a predetermined amount of fluid from the tip onto an analysis slide, and eject the tip after the metering operation.

14 Claims, 4 Drawing Figures

METHOD AND APPARATUS FOR METERING BIOLOGICAL FLUIDS

This application is a continuation-in-part of copending U.S. patent application Ser. No. 159,563, filed June 16, 1980, now abandoned.

CROSS-REFERENCES TO RELATED APPLICATIONS

Reference is made to commonly-assigned U.S. patent applications: Ser. No. 054,064, entitled Metering Apparatus, filed in the name of Jessop et al., on July 2, 1979; and Ser. No. 054,060, entitled Metering Apparatus, filed in the name of Jessop et al., on July 2, 1979.

BACKGROUND OF THE INVENTION

1. Field of the Invention

This invention relates to the chemical analysis of substances, and more particularly to a method and apparatus for the precise metering of biological fluids onto test elements.

2. State of the Prior Art

A number of automated systems have been developed for performing quantitative chemical analyses of fluid samples. Most of the commercially-available systems utilize liquid reagents and require analyzer equipment having intricate solution handling and transport capabilities. Recent developments, however, have provided test elements in essentially planar, dry form which can be loaded into a cartridge for use in an analyzer. In the use of such an analyzer, a test element from a cartridge is fed into a metering station where a predetermined amount of sample fluid is deposited on the test element. After an incubation period, the element is moved to a read station where a change in the test element is measured, the amount of change being proportional to a particular analyte in the fluid. The test element is used only once and is discarded after the reading has been taken. An analyzer for use with such test elements is disclosed in commonly-assigned U.S. Pat. No. 4,152,390.

Test elements of the type described above are adapted to function with very small quantities of sample fluid. For example, test elements for performing colorimetric analyses can produce a measurable response with only 10 microliters of sample fluid, and elements for performing potentiometric analyses are operable with 10 microliters of sample fluid and 10 microliters of reference fluid. The volume of fluid supplied to the elements should preferably not vary more than 5% from a selected value to achieve desirable test results. Thus, there is a problem in providing a metering device which can deliver precise micro quantities of fluid, in spite of variations in the physical properties of the fluid and the test elements. Moreover, in high-throughput analyzers, the metering device must be capable of repeatedly and accurately dispensing such quantities of fluid onto the test elements as they are sequentially moved into a metering station.

A metering device for use with planar test elements is shown in commonly-owned U.S. Pat. No. 4,142,656, to Smith et al. In this patent, fluid is dispensed from a sample cup having a dispensing tip formed on a bottom wall thereof. An electrically-actuated pump is used to generate a pressure in the cup sufficiently above ambient to form a pendant drop on the dispensing tip. The test element is then moved into contact with the pendant drop to effect a transfer of the fluid to the element. Both the sample cup and the test element are transported to the metering apparatus. The metering device disclosed in the Smith et al. patent requires complex transport and drive elements for both the sample cup and the test element, and it is not intended for use in applications where fluid must be aspirated into the metering device.

The patent to Drozdowski et al., U.S. Pat. No. 3,832,135, discloses a metering device which is adapted to pick up a disposable tip, aspirate fluid into the tip, meter fluid into a receptacle, and eject the tip. Drozdowski et al., however, do not contemplate the metering of fluids onto a series of analysis slides. The patent to Lightner, U.S. Pat. No. 3,988,921, shows apparatus for metering through a capillary tube onto a chromatographic plate. In the Lightner apparatus, the capillary tube is loaded with a quantity of fluid, and all of the fluid in the tube is dispensed onto a single plate. Since the tube must be reloaded for each new plate, the Lightner apparatus would not be suitable for use in a high-throughput analyzer where a series of tests are performed on a single sample fluid. Further, none of the known prior-art devices is directed to solving the problem of aspirating a fluid from a sample cup and depositing predetermined amounts of the fluid onto a plurality of analysis slides sequentially moved into a metering station.

SUMMARY OF THE INVENTION

It is an object of the present invention to overcome the above-described problem in prior-art devices, and to provide a novel method and apparatus for the repeated, precise dispensing of micro quantities of fluid onto test elements for the analysis of biological fluids. The invention is particularly applicable to the metering of biological fluids onto generally planar test elements, or analysis slides.

In accordance with one aspect of the invention there is provided metering apparatus for precisely dispensing a predetermined quantity of a biological fluid onto a plurality of generally planar analysis slides sequentially moved into a metering station, the slides being selected from more than one type and different types having different rates of absorption, the apparatus comprising: dispenser means including a metering tip having a fluid chamber for receiving fluid aspirated into the tip through an aperture therein, the chamber being sufficiently large to contain enough fluid for a plurality of the slides; pump means in fluid communication with the metering tip, the pump means being actuatable for a preselected period to expel fluid from the tip at a substantially constant dispense rate; and positioning means operatively connected to the dispenser means for moving the tip to a metering position adjacent to a slide in the metering station and spaced a sufficient distance from the slide such that fluid delivered at the dispense rate will flow in a continuous stream to the slide, the positioning means being adapted to withdraw the tip from the metering position a predetermined time after the period.

There is also disclosed a process for the precise dispensing of a biological fluid from a metering tip onto a generally planar analysis slide; the process comprising the steps of: aspirating the fluid into the tip until the tip is partially filled with fluid and has an air space above the fluid; positioning the tip in a metering position closely adjacent the slide and spaced therefrom between about 0.030 cm and about 0.15 cm; pressurizing the air and fluid in the tip for a preselected period to force about 10 µl of fluid onto the slide at a dispense rate of between about 10 µl/sec and 300 µl/sec; and maintaining the tip in the metering position between about 0.05 second and about 0.5 second after the period and then withdrawing the tip from the metering position.

In one embodiment of the invention, a dispenser having a disposable metering tip is supported on a carriage which is mounted on support rods for lateral movement. The dispenser is raised and lowered by means of a rack-and-pinion drive. At the start of a metering cycle, the carriage is moved to locate the dispenser over a waste receptacle where the metering tip from the preceding metering cycle is ejected. The dispenser then picks up a new metering tip, and a supply of sample fluid is aspirated into the tip. The dispenser means is then moved to position the tip in a metering position where a predetermined amount of sample fluid is deposited onto an analysis slide to complete the metering cycle.

In the event several different tests are desired on the same sample fluid, the metering tip is raised after each metering operation and lowered into the metering position for each new analysis slide. Cross-contamination from one sample fluid to another is eliminated, since sample fluid does not pass beyond the metering tip, and each metering tip is used for only one sample fluid.

The disclosed invention is adapted to deliver fluid to a slide with the desired precision and accuracy, in spite of substantial variations in the physical properties of the fluid. To achieve this result, applicants have found that several properties must be carefully controlled, including the spacing of the metering tip from the analysis slide, the rate at which the fluid is expelled from the tip, the dwell time of the metering tip in the metering position after the pump stops, and the rate at which the tip is withdrawn from the slide after completion of the metering operation.

DESCRIPTION OF THE PREFERRED EMBODIMENT

Figure 1:
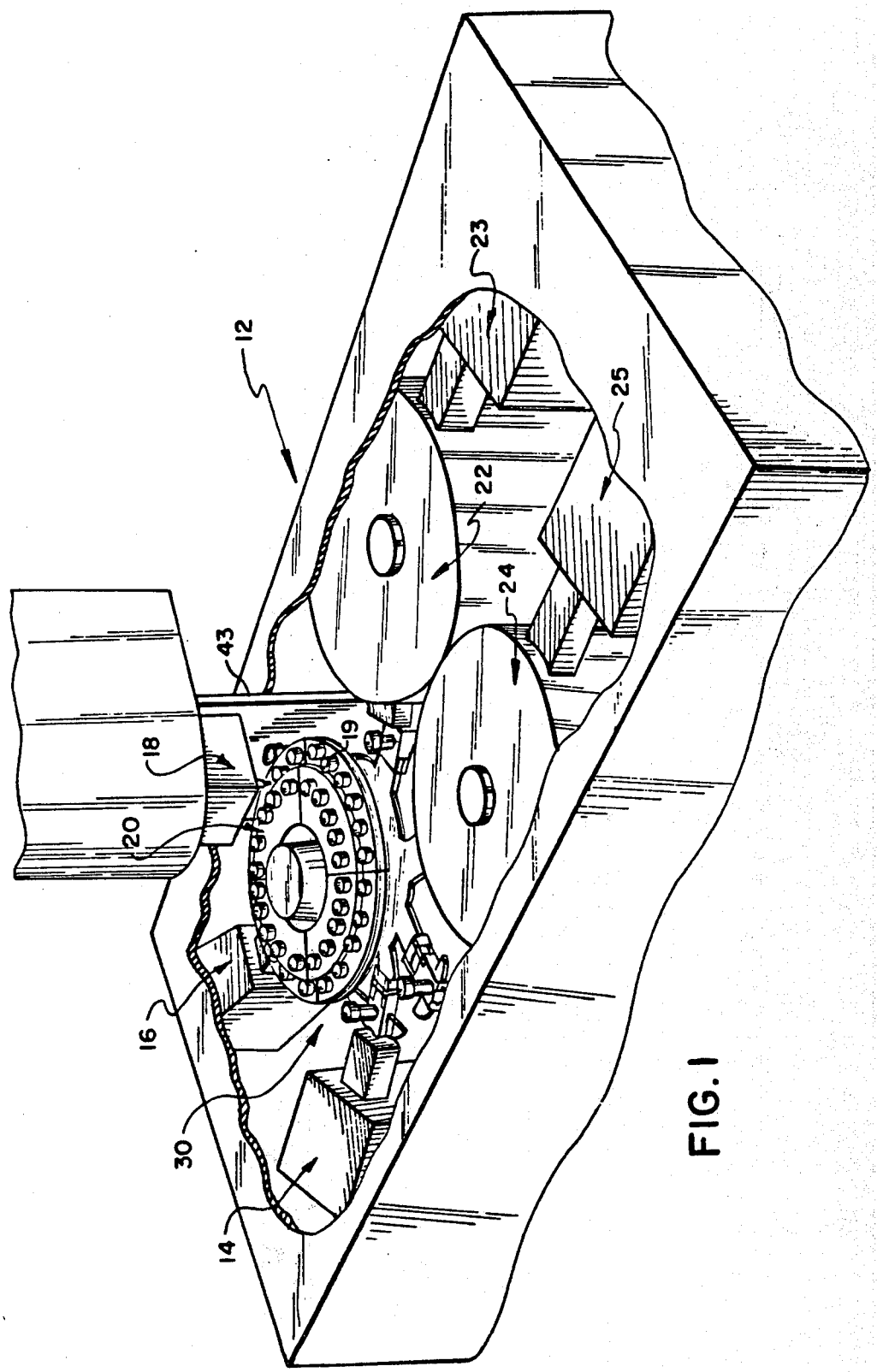
FIG. 1 is a perspective view of a chemical analyzer of the type which is adapted to employ the metering apparatus described herein.

The invention is described hereinafter in connection with an analyzer for performing quantitative chemical analyses of biological fluids, such as blood serum. However, the invention is not so limited, and it can also be employed in other types of apparatus where precise metering devices are required. Although the dispensing of blood sera is described hereinafter by way of example, the apparatus may be used to dispense fluid in any repetitive dispensing operation which requires that the amount of dispensed fluid be uniform in spite of substantial variation in physical properties of the sample fluid so dispensed.

One form of test element, or analysis slide, for use with the subject invention is disclosed in the commonly-owned U.S. Patent to Pryzbylowicz et al., U.S. Pat. No. 3,992,158, granted on Nov. 16, 1976. The test element disclosed in this patent is formed as a multi-layer element containing the necessary reagents for reaction with components of a biological fluid, such as blood serum, deposited thereon. Certain reactions colorimetrically produce a change in optical density in the element which is sensed by a reflectometer, the amount of light reflected from the element varying in accordance with the reaction and being indicative of the amount of a particular analyte present in the fluid. Another form of test element for use with the disclosed invention is shown in the patent to Hamblen et al., U.S. Pat. No. 4,053,381, granted Oct. 11, 1977. This patent describes a test element, or analysis slide, of the type which is used to potentiometrically designate the activity of ions in a liquid test solution by the use of electrodes.

The different forms of test elements usable with applicants' invention will vary to some degree in the absorption rates at which they attract fluid metered onto the element; this is due, in part, to a variance in the capillary action in the different forms of elements and to a wicking action between layers in certain elements. Because of this variance in the test elements, certain characteristics of applicants' invention, described hereinafter, must be carefully controlled to achieve the desired precision and accuracy.

Terms such as "up," "down," "lower," "vertical," "horizontal," and "bottom," as used herein, refer to the orientation of parts when the disclosed apparatus is positioned in its customary position of use.

The sera to be dispensed are to be tested by devices requiring very accurate, small volumes of sera. The volumes to be dispensed are substantially fixed for a particular application and range from 1 to about 30 microliters, and preferably between about 8 and about 13 microliters. Such small volumes permit the performance of multiple tests on a relatively small volume of serum from a patient; in the case of elderly or infant patients, only small volumes of blood are available for testing, and the smaller the volume needed for each test, the greater the number of tests which can be run on a given sample of serum.

In accordance with the preferred embodiment of the invention, there is shown in FIG. 1 an analyzer 12 of the type which is adapted to employ a metering apparatus 18, described in detail hereinafter. Analyzer 12 comprises a slide supply 14 for analysis slides 15 of the colorimetric type (FIG. 2), and a slide supply 16 for analysis slides of the potentiometric type, not shown. Metering apparatus 18 is adapted to aspirate sample fluid from a cup 19 supported in a sample tray 20 and to deposit a predetermined amount of the fluid onto an analysis slide supported in a slide distributor 30. A second metering device, not shown, works in conjunction with metering apparatus 30 to also deposit reference fluid on analysis slides of the potentiometric type. After the metering operation, analysis slides of the potentiometric type are deposited in an incubator 22 by distributor 30, and analysis slides of the colorimetric type are deposited in an incubator 24. Incubators 22, 24, are adapted to cooperate respectively with analysis means 23, 25, for measuring a change in the analysis slides as a result of the fluids deposited thereon.

Figure 2:
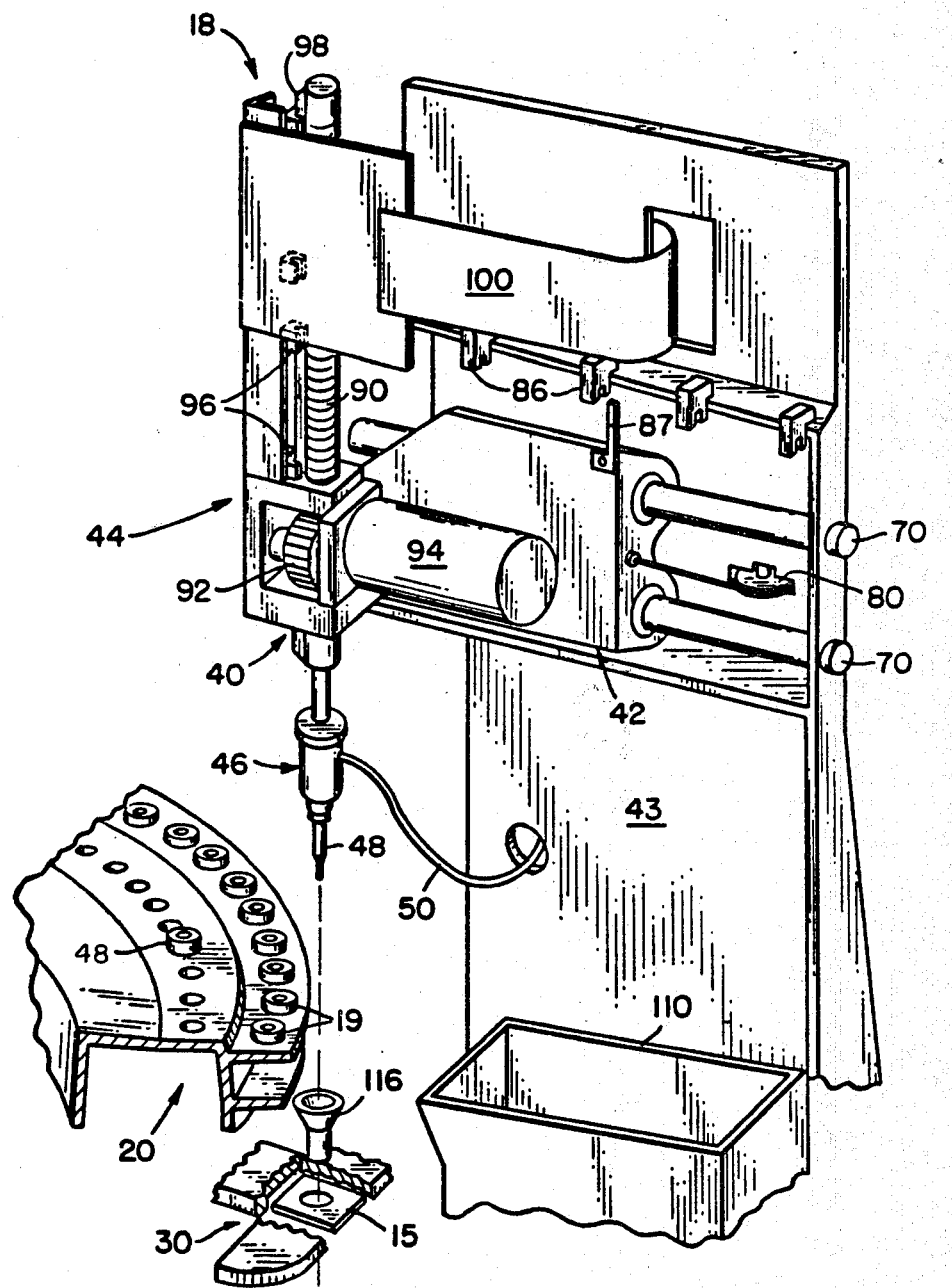
FIG. 2 is a perspective view of the metering apparatus of the subject invention, showing the dispenser and the carriage for the dispenser.
Figure 3:
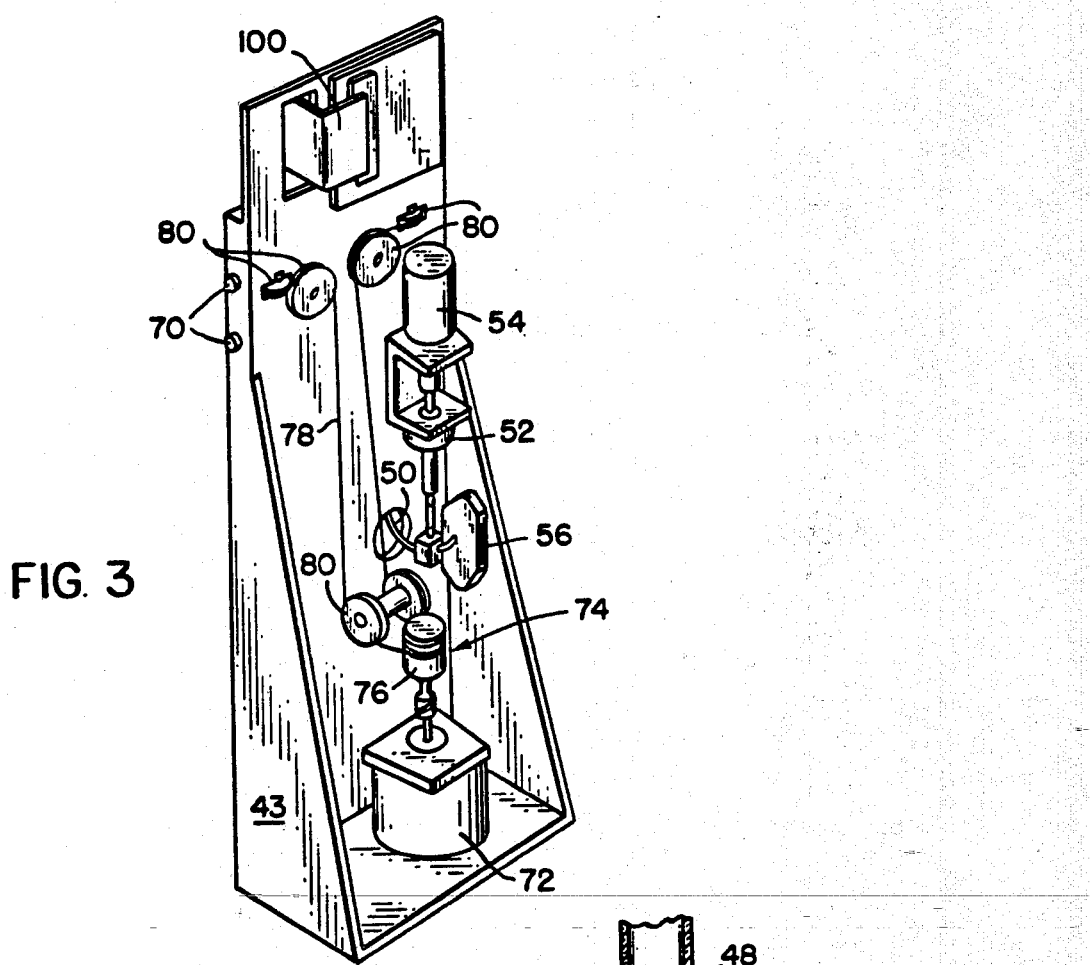
FIG. 3 is a perspective view of a pump for the dispenser and a drive mechanism for the carriage.

With reference to FIG. 2, metering apparatus 18 comprises a dispenser 40 and a means for positioning dispenser 40 which includes a carriage 42 for moving dispenser 40 laterally through a plurality of stations in analyzer 12, and a vertical drive 44 for raising and lowering dispenser 40 at each of the stations. Dispenser 40 comprises a dispenser head 46 which is adapted to receive a disposable metering tip 48, and is connected by means of a line 50 to a pump 52 (FIG. 3) of the positive displacement type. Pump 52 comprises a piston, not shown, which is driven by a bidirectional stepper motor 54.

When motor 54 is actuated in one direction, a partial vacuum is created in line 50 by pump 52, and fluid is drawn into tip 48 until the tip is partially filled. Motor 54 is actuated in an opposite direction to meter fluid from tip 48. In the metering operation, motor 54 drives pump 52 for a preselected period during which the pressure in line 50 and tip 48 is raised sufficiently to force about 10 μl of fluid onto an analysis slide. Under certain operating conditions, depending on the amount of fluid aspirated into tip 48, it may be desirable to vent line 50 before dispensing fluid onto an analysis slide. A pressure transducer 56 closely monitors pressure in line 50 for purposes which will be explained in more detail hereinafter.

Sample tray 20 is adapted to carry a disposable tip 48 for each of the sample fluids to be analyzed. A new tip 48 is used with each sample fluid to avoid any cross-contamination problems. The cups 19 containing sample fluid are arranged around the outer periphery of tray 20, as shown in FIG. 2. An indexing mechanism, not shown, advances tray 20 at the start of each metering cycle to bring a cup 19 and new tip 48 respectively into the aspiration station and the tip supply station for cooperation with metering apparatus 18. Tips 48 can be formed by known molding techniques from polymers, such as acetal and polypropylene. One tip which is particularly suitable for use in apparatus 18 is the tip described and claimed in commonly-owned U.S. application Ser. No. 168,789, filed on July 14, 1980, by R. L. Columbus, entitled "Self Cleaning Nozzle Construction for Aspirators." Also, certain commercially-available pipette tips have metering characteristics which are acceptable for use in apparatus 18. One example of such a tip is the Elkay #000-000-01C tip, manufactured by Elkay Products, Inc., Worcester, Mass.

Carriage 42 is mounted for horizontal movement on two parallel support rods 70. Rods 70 are carried on a pylon 43 attached to the analyzer frame, not shown. A drive means for carriage 42 includes a bidirectional stepper motor 72 (FIG. 3) which is connected to a capstan drive 74. Drive 74 comprises a drum 76; a cable 78 carried on drum 76 is supported on guide pulleys 80 and connected to carriage 42. It will be seen from FIGS. 2 and 3, that when motor 72 is driven, for example, in a counterclockwise direction, as viewed in FIG. 3, carriage 42 will move to the right (FIG. 2). Carriage 42 must be located along a line at four points which include the tip pick-up station, the aspiration station, the metering station and the tip-eject station. Four horizontal-position sensors 86 of a photoelectric type cooperate with a flag 87 on carriage 42 to precisely position the carriage 42 at each of these stations.

Vertical drive 44 comprises a rack 90 which is attached to dispenser head 46. Rack 90 is raised and lowered by means of a pinion 92 driven by a stepper motor 94 mounted on carriage 42. Four vertical-position sensors 96 cooperate with a flag 98 on rack 90 to precisely determine the vertical position of dispenser head 46. Power from a power supply, not shown, is supplied to the sensors 96 and motor 94 through a ribbon cable 100.

In the operation of metering apparatus 18, dispenser 40 is moved through at least one complete metering cycle for each sample fluid. At the start of the metering cycle, carriage 42 is moved to the tip-eject station to position dispenser 40 over a waste receptacle 110 where a metering tip 48 from a previous metering cycle is ejected into the receptacle 110 by an ejector, not shown, on head 46. Carriage 42 is then moved by motor 72 to the tip-supply station where dispenser 40 is located directly over a disposable tip 48 in sample tray 20. Dispenser 40 is then lowered to pick up a tip 48, raised, and moved laterally to the aspiration station. Dispenser 40 is then lowered to locate a tip 48 in a sample cup 19 where it aspirates sufficient sample fluid to perform the number of tested desired. After aspiration and before withdrawal of the tip 48, approximately 10 μl of fluid are dispensed back into cup 19; this primes the dispenser and insures that the first analysis slide will receive a precise amount of fluid. The dispenser 40 is then raised, moved laterally to the metering station where tip 48 is positioned directly over an analysis slide 15; tip 48 is then lowered into a guide 116 (FIG. 2) on distributor 30 which locates the tip 48 in the metering position. Pump 52 is then actuated for a preselected period to meter the desired amount of sample fluid onto the analysis slide 15. Tip 48 remains in the metering position for a predetermined time after pump 52 stops to complete the metering operation; then dispenser 40 is raised to a home position, shown in FIG. 2. In most cases, more than one analysis will be performed per sample fluid. If additional analyses are being performed, the dispenser 40 will be raised and lowered for each new slide.

Metering apparatus 18 is particularly suitable for use with biological fluids, e.g. blood serum having a surface tension which varies between about 28 dynes/cm and about 75 dynes/cm and a relative viscosity between about 0.8 and about 3 (compared to distilled water). Apparatus 18 is adapted to dispense these fluids such that the mean metered volume does not vary more than 5% from a selected value, and the precision, expressed as a coefficient of variation, is less than 5%. To achieve these results, metering apparatus preferably has the properties listed below.

Figure 4:
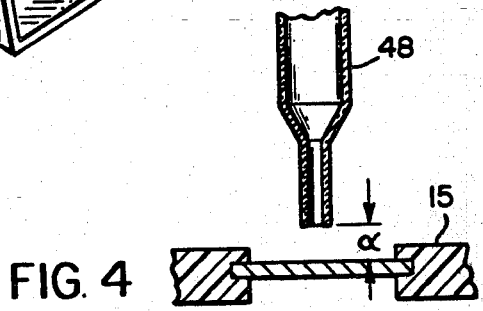
FIG. 4 is an enlarged elevational view, partially in section, showing a metering tip in the metering position over an analysis slide.

1. There should be no separation of the fluid stream during the metering operation. To make sure that separation does not occur it has been found that the spacing $\alpha$ of tip 48 from slide 15 (See FIG. 4) is preferably between about 0.012 inches (0.030 cm) and about 0.060 inches (0.15 cm).

2. It is also preferred that the dispense rate at which fluid is expelled from tip 48 is between about 10 μl/sec and about 300 μl/sec. If the dispense rate is too slow, there is danger of separation of the fluid stream, even with proper spacing of tip 48 from slide 15; if the rate is too fast, fluid tends to build up around tip 48. A representative rate within this range is 50 μl/sec, which can be used regardless of the type or chemistry of the slide onto which the fluid is being metered. That is, this fixed, predetermined rate has been used both on colorimetric type slides, e.g. glucose, BUN, or a like assay, as well as on potentiometric slides, e.g. a NA+ assay.

3. At the completion of the dispensing of fluid, i.e. after pump 52 has stopped, it is preferred that tip 48 dwell in the metering position (FIG. 4) between about 0.05 sec and about 0.5 second before being withdrawn. This insures that there will be a clean break of the stream of fluid upon withdrawal; if the tip dwells for a greater period of time, fluid may be pulled out of tip 48 by the slide.

4. After the dwell time as noted above, it is preferred that tip 48 be withdrawn from the metering position at a rate of between about 0.2 inches/sec (0.5 cm/sec) and about 2 inches/sec (5.08 cm/sec). The tip 48 is withdrawn at a relatively slow rate to allow a fluid wipe-off effect.

In the use of the disclosed metering apparatus with a high-throughput analyzer, as shown in FIG. 1, a metering operation takes place approximately every 12 seconds. Thus, it will be seen that each of the steps in the metering cycle must be carefully controlled and monitored, and metering apparatus 18 must function in timed relation to other elements of analyzer 12. Pressure transducer 56 is used to monitor the performance of apparatus 18. Pressure is sensed in line 50, and if conditions are present such as a plugged tip 48, no fluid in cup 19, or a separation of the fluid stream between the tip 48 and the slide 15, they will be detected by the transducer. A control system (not shown) for metering apparatus 18 could include one or more computers which may take any of the various forms known in the art that include programmable microcomputers. The instructions and method of programming such computers is well known in the art, and thus, no further explanation is considered necessary.

The invention has been described in detail with reference to certain preferred embodiments thereof, but it will be understood that variations and modifications can be effected within the spirit and scope of the invention.

What is claimed is:

1. Metering apparatus for precisely dispensing a predetermined quantity of a biological fluid onto a plurality of generally planar analysis slides sequentially moved into a metering station, said slides being selected from more than one type and different types having different rates of absorption, said apparatus comprising:
   dispenser means including a metering tip having a fluid chamber for receiving fluid aspirated into the tip through an aperture therein, said chamber being sufficiently large to contain enough fluid for a plurality of said slides;
   pump means in fluid communication with said metering tip, said pump means being actuatable for a preselected period to expel fluid from said tip at a substantially constant dispense rate; and
   positioning means operatively connected to said dispenser means for moving said tip to a metering position adjacent to a slide in the metering station and spaced a sufficient distance from the slide such that fluid delivered at said dispense rate will flow in a continuous stream to said slide, said positioning means being adapted to withdraw said tip from said metering position a predetermined time after said period.

2. Metering apparatus, as defined in claim 1, wherein said dispense rate is between about 10 μl/sec and about 300 μl/sec.

3. Metering apparatus, as defined in claim 1, wherein said distance is between about 0.030 cm and about 0.15 cm.

4. Metering apparatus, as defined in claim 1, wherein said time is between about 0.05 second and about 0.5 second.

5. Metering apparatus, as defined in claim 1, wherein said positioning means is adapted to withdraw said tip at a rate of between about 0.5 cm/sec and about 5.08 cm/sec.

6. Metering apparatus, as defined in claim 1, wherein said quantity of fluid is about 10 μl.

7. Metering apparatus, as defined in claim 1, wherein said fluid has a surface tension within the range from between about 28 dynes/cm to about 75 dynes/cm.

8. A process for the precise dispensing of a biological fluid from a metering tip onto a generally planar analysis slide, said process comprising the steps of:
   aspirating the fluid into said tip until the tip is partially filled with fluid and has an air space above the fluid;
   positioning the tip in a metering position closely adjacent the slide and spaced therefrom between about 0.030 cm and about 0.15 cm;
   pressurizing the air and fluid in the tip for a preselected period to force about 10 μl of fluid onto the slide at a fixed, predetermined dispense rate of between about 10 μl/sec and 300 μl/sec; and
   maintaining said tip in the metering position between about 0.05 second and about 0.5 second after said period and then withdrawing the tip from said metering position.

9. A process, as defined in claim 8, wherein said tip is withdrawn from the metering position at the rate of between about 0.5 cm/sec and about 5.08 cm/sec.

10. Metering apparatus for use in an analyzer for the analysis of biological fluids, said apparatus being adapted to meter a predetermined quantity of fluid onto an analysis slide for the testing of a particular analyte, said analyzer being adapted to measure a change in said slide which is indicative of the amount of analyte in said fluid, said apparatus comprising:
   means for supporting said slide in a metering station;
   dispenser means including a metering tip having a fluid chamber for receiving fluid aspirated into said tip through an aperture therein;
   pump means in fluid communication with said metering tip; said pump means being adapted to aspirate fluid into said tip and to expel fluid therefrom in precise amounts;
   carriage means for moving said dispenser means laterally through a plurality of stations in the analyzer; and
   drive means for raising and lowering said dispenser means at each of said stations, said drive means being adapted to move said dispenser means independently of said carriage means.

11. Metering apparatus, as defined in claim 10, wherein said dispenser means comprises a dispenser head for receiving said tip and a pressure detecting means in fluid communication with said tip is connected to said dispenser head.

12. Metering apparatus, as defined in claim 10, wherein said pump means comprises a positive displacement pump and a stepper motor connected to said pump.

13. Metering apparatus, as defined in claim 10, wherein said carriage means comprises a carriage movably supported on generally parallel support rods, and a capstan drive connected to said carriage.

14. Metering apparatus, as defined in claim 10, wherein said drive means comprises a rack and pinion operatively connected to said dispenser means.

* * * * *